United States Patent [19]

Sneider

[11] Patent Number: 4,591,357

[45] Date of Patent: May 27, 1986

[54] CONTAINER FOR DRUG ISOLATION, STORAGE AND SUBSEQUENT MIXING

[76] Inventor: Vincent R. Sneider, 3422 Hallcrest Dr., Atlanta, Ga. 30319

[21] Appl. No.: 780,997

[22] Filed: Sep. 27, 1985

[51] Int. Cl.[4] ........................ B65D 30/22; A61M 5/00

[52] U.S. Cl. ...................................... 604/416; 604/89; 604/410; 206/221

[58] Field of Search .................. 604/89, 91, 408, 410, 604/416; 206/219, 221

[56] References Cited

U.S. PATENT DOCUMENTS

| | | | |
|---|---|---|---|
| 2,753,868 | 7/1956 | Seemar | 604/416 X |
| 3,163,163 | 12/1964 | Wilburn | 206/221 |
| 3,842,836 | 10/1974 | Qgle | 206/221 X |
| 4,315,570 | 2/1982 | Silver et al. | 206/221 |
| 4,410,321 | 10/1983 | Pearson et al. | 206/56 |
| 4,458,811 | 7/1984 | Wilkinson | 206/219 |
| 4,462,224 | 7/1984 | Dunshee et al. | 206/219 X |

*Primary Examiner*—Stephen C. Pellegrino

*Attorney, Agent, or Firm*—Ralph R. Roberts

[57] ABSTRACT

A drug-mixing device is shown and provides a substantially rectangular envelope of flexible plastic. This envelope retains the drug diluent and a concentrate container in a selectively closed condition. The intermediate portions of the envelope are sufficiently flexible to be captured between a lower projecting ring on the bottle and a lower pull tab of resilient material. The upper end of the concentrate container is closed by a resilient cap having a ring thereon. An upper pull tab of resilient material is adapted to be secured to this cap, with an upper portion of the flexible envelope therebetween. Orienting means is provided in the end portions of the bottle and the cap so that rotation as well as lifting of the cap may be achieved with no rupture of the flexible walls of the envelope. Grippping areas are provided on both ends of the envelope for shake mixing. Withdrawal of the mixed drug is conventionally achieved by a syringe and needle through a neck and cover film on the envelope.

20 Claims, 7 Drawing Figures

CONTAINER FOR DRUG ISOLATION, STORAGE AND SUBSEQUENT MIXING

BACKGROUND OF THE INVENTION

1. Field of the Invention

In accordance with the classification of art as established in and by the U.S. Patent Office, this invention is believed to pertain to special containers and also to the mixing of potent drugs as found in the general class of "Surgery." This drug isolation and mixing device utilizes a flexible bag in which the diluent is placed. About midway of the device is mounted a glass vial having a special configuration and a cover member. Removal of the cover while still within the bag enables the drug to be mixed with the diluent for subsequent injection into a patient.

2. Description of the Prior Art

A careful pre-Ex search was made in the files of the U.S. Patent Office and although drug mixing and packages for such drugs were noted, the concept of storing the potent drug in an impervious container with a removable cap as provided by applicant was not found. A drug isolation device was the subject of U.S. Pat. No. 1,585,911 to Heublein as issued May 25, 1926. This patent illustrated a glass ampule having two compartments and having in one compartment a liquid and in the other the drug (usually a powder). A lever portion is manipulated to break a stem portion and allow the fluid to enter the drug compartment where it is mixed. The ampule is broken to the extent that this mixed drug is removed usually by a syringe. The objection to this device is the potentiality of broken glass and the possibility of exposure to the practitioner.

Also of note is U.S. Pat. No. 3,163,163 to Wilburn, as issued Dec. 29, 1964. This patent shows a container with a reduced center portion in which is tightly secured a rubber stopper. This stopper is displaced into the lower container portion and permits the two portions to be intermixed. This invention requires a container having at least a partially deformable resilient top portion that utilizes the fluid in this upper portion to assist in the displacement of the stopper. It is to be noted that the stopper may be displaced by accidental pressure. Not mentioned is that fluids tend to pass through resilient stoppers when they provide the barrier wall as shown in FIG. 1 or 4 of U.S. Pat. No. 3,163,163.

A two-compartment container is provided in U.S. Pat. No. 4,315,570 to Silver et al., as issued Feb. 16, 1982. This patent also utilizes a plunger and a stopper moved by this plunger. The lower end seal as shown in FIGS. 3 and 4 is mounted on the plunger and additionally provides a deflector which, according to the teaching, promotes dispersion of the powder for enhancement of mixing.

Also noted is U.S. Pat. No. 4,410,321 as issued to Pearson et al. on Oct. 18, 1983. This storage system is a closed system with separate compartments. This device utilizes a needle to penetrate a stopper and through this needle is carried the concentrate. This system is for a mixed-drug delivery system using known intravenous administrative procedures. This system as exemplified in U.S. Pat. No. 4,410,321 is rather elaborate and is not adapted for use in other than intravenous applications and systems.

U.S. Pat. No. 4,462,224 was also noted. This patent issued to Dunshee et al. on July 31, 1984 and shows a flexible plastic bag with rupturable seams. When the seam is ruptured, then the contents of three compartments are mixed to provide instant hot or cold any may be reused. This device, although employing an envelope of flexible plastic, does not contain the potent drug portion in a glass retainer as does applicant's.

These prior art examples do not address the problem faced with the newly-available drugs, particularly cancer-treating drugs. Most of these drugs need to be mixed immediately or shortly before use. Many of the resulting mixed drugs are very toxic, even to the administrator of the drug, so that contact is very undesirable. Rubber gloves may be punctured or otherwise do not provide the needed protection. The invention to be described and as shown overcomes the objections to the prior art devices.

SUMMARY OF THE INVENTION

This invention may be summarized, at least in part, with reference to its objects. It is an object of this invention to provide, and it does provide, a drug-mixing device in which the diluent and drug concentrate are positively separated until time for mixing. The concentrate is then opened to the diluent only through grasping and manipulation by and with two hands. The mixed drug is withdrawn by a syringe and needle through an access cap closure member.

It is a further object of this invention to provide, and it does provide, a flexible bag container for storage of the diluent. The near midportion is configured with a recess portion in which there are provided portions specially formed to enable engaging lip portions on a closed end of the rigid container for the drug concentrate to be engaged by a tap member mounted on the exterior of the container. The flexible container portion is retained between the end of the concentrate container and the tab member. The cover cap of the concentrate member is also formed with a protruding rim which is gripped by a pull tab exteriorally mounted. The flexible container portion is retained between the cap and pull tab so as to retain the fluid contents before, during and after mixing.

In brief, the drug-mixing device of this invention contemplates forming, as by blow molding and the like, an outer envelope of flexible plastic. This outer envelope is adapted to retain liquid for extended periods of time. This liquid is the desired diluent for the drug and when and as the drug is mixed, usually by shaking, the envelope is unaffected by this mixed drug. The drug concentrate may be in powder, semi-liquid or liquid form and usually is a small quantity of one ounce or less. The drug either in concentrate or in mixed form is often toxic to the administrator so exposure is usually avoided and avoidance is desired. As shown in the drawings, grasping and manipulation for the concentrate container and cap is by tab members which are specially configured to provide separation while maintaining the integrity of the envelope. The mixed drug is conventionally removed through a pierceable cover valve or a filling spout or neck. The pull or lift tab is shown with and without a strap portion for grasping by the administrator.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there has been chosen a specific embodiment of a container for isolation, storage and mixing of the components as adopted for use in a flexible plastic container and showing a preferred means for containing the drug concentrate in a glass container with removable cap tab members. This specific embodiment and an alternate pull tab have been chosen for the purposes of illustration and description as shown in the accompanying drawings wherein:

BRIEF DESCRIPTION OF THE DRAWINGS

In the following description and in the claims, various details are identified by specific names for convenience. These names are intended to be generic in their application. Corresponding reference characters refer to like members throughout the several figures of the drawings.

The drawings accompanying, and forming part of, this specification disclose details of construction for the purpose of explanation, but structural details may be modified without departure from the concept and principles of the invention and the invention may be incorporated in other sturctural forms than shown.

EMBODIMENT OF FIGS. 1 AND 2

Figure 1:
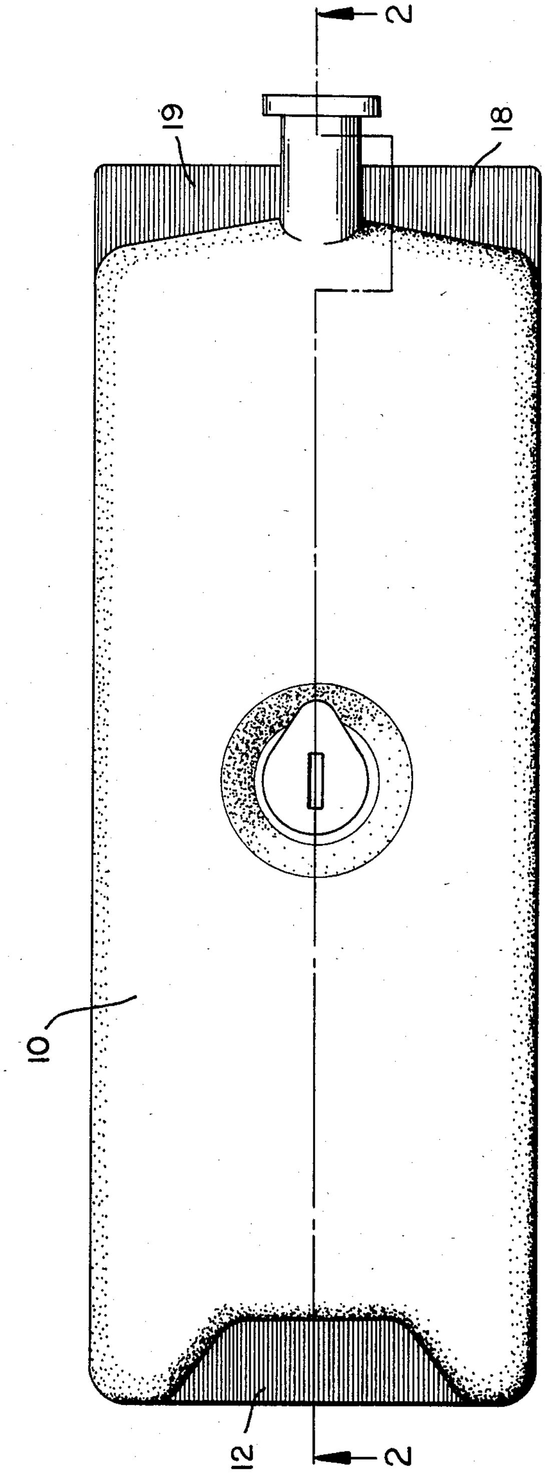
FIG. 1 represents a plan view, partly diagrammatic, and showing substantially in full size the drug storage, separation and mixing device of this invention.
Figure 2:
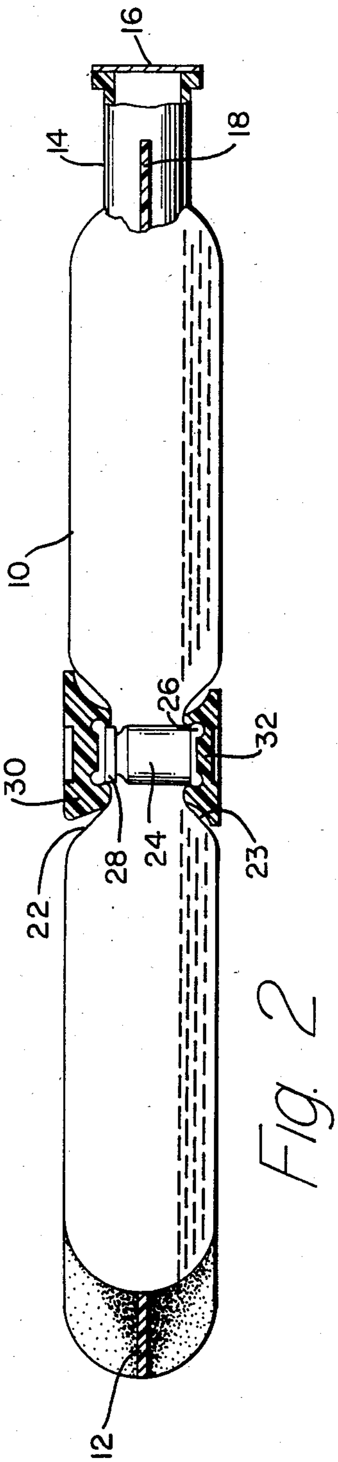
FIG. 2 represents a side sectional view of the storage, separation and mixing device of FIG. 1, this view taken on the line 2—2 thereof and looking in the direction of the arrows.

Referring next to the drawings and the showing of FIGS. 1 and 2, there is depicted an assembled device ready for shipping but with the cap not removed for mixing. An envelope 10 is contemplated to be of molded flexible plastic and having a selected shape and, as shown, the envelope has a generally rectangular configuration. The left end has a ribbed grip portion 12 which is adapted to be grasped by an attendant at the time of shaking and thorough mixing. The other end has a neck portion 14 which is shown as generally central and provides a passageway from the exterior to the inner chamber of the envelope. As seen in section, the outer end of the neck portion 14 is closed by a closure member 16. It is contemplated that this closure member 16 is attachable in a secure manner such as by a shrink-wrap band, cement or the like. It is desired that this closure member be able to be penetrated by a sharpened needle and, if desired, be capable of its resealing with the withdrawal of the needle. As shown, the receptacle is about three-fourths size, but this is merely a matter of selection. It is to be noted that positioned on either side of the neck 14 are gripping areas 18 and 19.

The central portion of envelope 10 is formed with areas generally identified as 22 and 23. The upper formed area portion is identified as 22 and the lower portion is identified as 23. Seen in FIG. 2 is a bottle, generally identified as 24. This bottle is contemplated as of glass with a bottom portion having an outward-extending ring portion 26. This bottle is more clearly seen in FIGS. 3 and 5. This bottle 24, after filling with a concentrated drug portion of a determined quantity, is closed by and with a stopper or cap 28 which is conventionally of rubber or a rubber-like material having resilient properties. As fluid tends to pass through rubber or similar material, it is contemplated that the interior surface of this cap have a Mylar (TM DuPont) or like attached film member that is impervious to fluid migration. In FIGS. 1 and 2 is shown an upper pull tab 30 that is used by the practitioner to remove the cap 28. A lower pull tab 32 is also shown to grip the bottle 24 during removal of the cap.

EMBODIMENT OF FIG. 3

Figure 3:
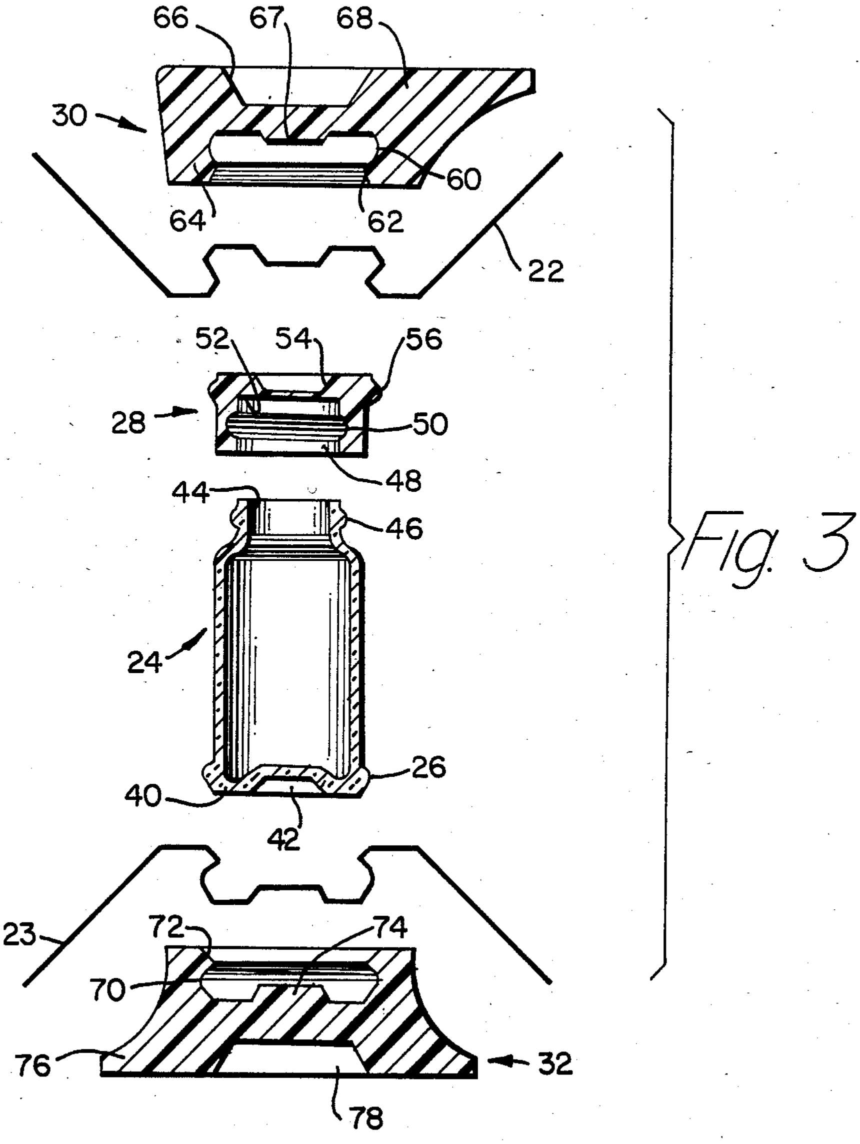
FIG. 3 represents an exploded side sectional view, partly diagrammatic, and showing the arrangement of components for containing and opening the drug concentrate container.

FIG. 3 is partly diagrammatic and in the exploded condition is shown the relationship of the members for removal of the cap 28. As depicted, the bottle 24 is of glass and is molded to provide a bottom closed end 40 in which an orienting slot 42 is formed. This slot is more clearly shown in FIG. 4. In molding this glass bottle, the protruding ring 26 is made, more or less, of a precise size and configuration. The other end of this bottle is made with an open and reduced portion 44 on the exterior of which is molded a ridge or circumferential bead 46. Although depicted in an open condition, the drug concentrate is placed in the glass container or bottle 24 before cap 28 is mounted thereon. This cap is sufficiently resilient to be manipulated for removal from the bottle. This cap 28 has an internal recess 48 and a mid-portion retaining groove 50. An upper internal surface 52 has the added film barrier and when the cap is seated on the neck of the bottle, this barrier 52 is tightly urged into engagement with the open end of this neck. The top of this cap is formed with an orienting recess 54 which is usually a rectangular slot of a determined depth. Filling and closing of the bottle 24 is conventional before filing of the envelope with diluent. This cap, like the bottle, has a protruding bead or ring 56 which provides a gripping and retaining means.

As depicted, the filled bottle 24 may be inserted through neck portion 14 or a ribbed portion 12, 18 or 19 may be left open for insertion and positioning of the closed bottle before the envelope 10 is closed to provide a fluid container. The closing of the envelope is a matter of assembly-line technique. As seen in FIG. 3, the upper and lower film portions 22 and 23 are brought to the filled container and upper and lower pull tab members 30 and 32 are used to form and retain these envelope portions 22 and 23 therebetween. FIG. 3 is a more-or-less diagrammatic showing of the preferred relationship and retention of the filled bottle.

With the cap 28 in desired position on the bottle 24, the top pull tab, generally identified as 30, engages portion 22 so that recess 60 engages and retains the film portion 22 and bead 56 of the cap. To assist in positioning and placement of this tab, a flare 62 is provided that serves two purposes—this flare reduces positioning difficulties, and also provides a reduced, less-than-sharp, angle from the recess 60 to the inner flat surface 64 of the pull tab 30. An orienting indicator 66 is formed in this pull tab 30. Opposite indicator 66 there is formed an inwardly-extending tongue portion 67 adapted to enter and engage the orienting recess 54 formed in the cap 28. A manipulative tab portion 68 is provided to enable grasping thereof by an attendant.

The bottom of the bottle 24 is captured and retained in a like manner by tab member 32. The bottom of tab portion 32 is depicted as having a circular recess 70 adapted to grip and retain bead ring 26 on the bottle 24. The film portion 23 is retained therebetween. As in the pull tab 30, described above, the recess 70 is adjusted a flare 72 that is adapted to assist in placement. A tongue-like orienting device 74 is also provided in this tab portion 32. It is also to be noted that the bottom portion is caused to be flared outwardly at 76 to provide easier grasping and manipulation of member 32. An indicating grooved recess 78 is also provided in this member 32.

EMBODIMENT OF FIG. 4

Figure 4:
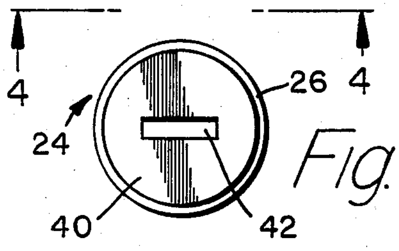
FIG. 4 represents a diagrammatic bottom view of the drug concentrate container and showing contemplated orienting means, this view taken on the line 4—4 of FIG. 5 and looking in the direction of the arrows.

In FIG. 4 is seen the bottom view of molded bottle 24. As depicted, bead 26 is shown as extending beyond bottom 40. In this molding there is formed a rectangular recess 42 which is configured and sized to receive the tongue 74 provided on and by tab 32 as it is molded.

EMBODIMENT OF FIG. 5

Figure 5:
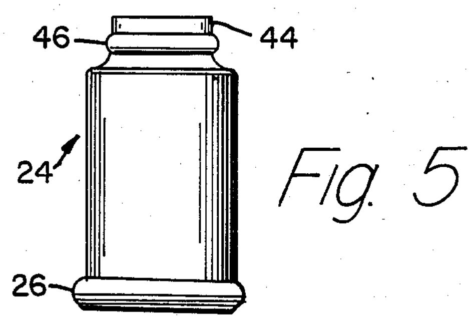
FIG. 5 represents a side view of the drug concentrate container.

In FIG. 5, the bottle 24 is in side view and the lower bead 26 is seen, as well as neck portion 44 on which is molded circular bead portion 46. Although glass is a cheap, impervious material for most, if not all, drug concentrates, this is not to preclude the use of other moldable materials, including some plastics and metals. The composition of this bottle is a matter of the drug concentrate to be retained therein.

EMBODIMENT OF FIG. 6

Figure 6:
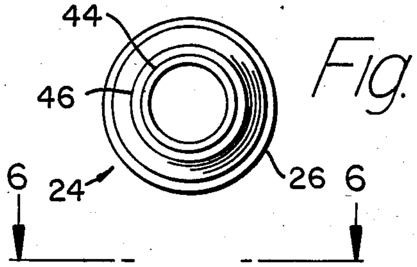
FIG. 6 represents a top view of the container of FIG. 5, this view taken on the line 6—6 thereof and looking in the direction of the arrows.

In FIG. 6, the bottle 24 is shown with the cap removed and looking downward on the bottle. As viewed, the lower ring 26 is seen and also the top ring 46 formed on the neck portion 44. The cap 28 for this bottle is shown in FIG. 3.

EMBODIMENT OF FIG. 7

Figure 7:
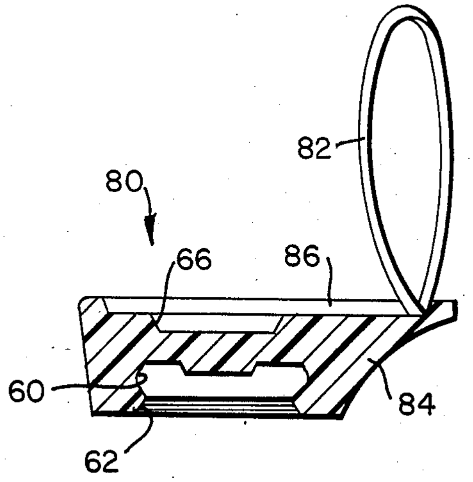
FIG. 7 represents a side sectional view of an alternate cap pull tab having a flexible strap means included therewith.

Referring next, and finally, to FIG. 7, there is depicted a side view, partly diagrammatic, of an alternate pull tab 80 for removing the cap from the bottle. This pull tab 80 is substantially like member 30 shown in FIG. 3, having recess 60, flare 62 and orienting indicator 66 very much as in FIG. 3. Rather than a manipulative portion 68 as in FIG. 3, there is additionally provided a loop member 82 which is integral with an extending portion 84. This loop portion is formed as indicator 66 is molded and a portion 86 of this tab member is formed in the top of this pull tab as indicated in this view. The loop member 82 provides added grasping means for the practitioner as he or she removes the cap 28 from the bottle 24.

USE AND OPERATION

It is anticipated that the bottle 24 is filled with a concentrate which is a powder, semi-fluid or fluids in the amount desired. The cap 28 is secured to the top of this bottle. The bead 46 is seated in groove 50 of the cap 28, with the barrier film 52 preventing unwanted penetration of the diluent into the bottle. After closing the bottle with the drug concentrate therein, this closed bottle is positioned within the envelope 10. The upper and lower portions 22 and 23 are brought to the bottle and the upper and lower pull tabs 30 and 32 are mounted in place. It is to be noted that the orienting slots 42 and 54 are positioned so that tongue portions 67 in the upper pull tab 30 and 74 in the lower tab 32 enter are are seated so that manipulation may be performed. These engaged orienting slots enable the practitioner to turn the cap 28 in relation to the bottle 24. This may be necessary before removal of the cap 28 from the bottle.

After the bottle has been inserted into position in the envelope 10, diluent is inserted into the envelope. This inflow of diluent is either through the neck portion 14 or through a rib portion before sealing. The inflow of diluent may be achieved by any convenient method and no patentable distinction is ascribed thereto. After filling the cavity of the envelope with the diluent, the seal 16 prevents escape until mixing is achieved. The upper and lower tab members 30 and 32 are grasped and twisting is usually used to loosen the cap 28 from the top of the bottle 24. The cap 28 is now tilted so as to cause recess 50 to be dislodged from the rib 46. Further manipulation and/or lifting causes the cap 28 to be lifted from the top of the bottle, after which the diluent is flowed into the bottle and the concentrate and diluent are mixed, usually by shaking. The envelope portions 22 and 23 are not punctured during this manipulation and mixing is achieved easily by grasping portions 12, 18 and/or 19. Since the mixed drug is usually quite toxic, removal of the mixture is usually by a needle and syringe, not shown but quite conventional.

This drug mixing device is made easily and provides shipping and storage prior to mixing, with the mixing usually just prior to use. The mixed drug may be removed through the end closure 16 or, if desired, through a piercing of the envelope 10. The pull tab 32 allows the practitioner to agitate the bottle 24 to insure that the concentrate is dispersed in the diluent. It is to be noted that the bottle 24 does not impede the transfer flow of diluent or mixed fluids from right to left and vice versa.

The drug-mixing device as shown in the drawings provides novel means of forming and assembling. The steps of manufacture of the drug-mixing device include:

forming of plastic an envelope of a material that is substantially impervious to unwanted escape or seepage and sized to retain a desired quantity of diluent, said envelope also formed with lower and upper midportions of flexible thicknesses and material so that said midportions are deformable and manipulable without rupture;

providing a fluid input and output pathway in said envelope so as to carry fluid to and from said envelope;

carrying and positioning a drug concentrate container within said envelope, said container of substantially rigid material and having an open neck portion with cap retaining means formed on this neck portion, this container also having a closed end formed with an outwardly-extending ring portion and in this closed end forming an orienting means for controlled rotational movement;

forming and providing a resilient cap or stopper and carrying said cap within the envelope, said cap formed with a retaining means compatible with and shaped to snugly engage and seat on the neck of the drug concentrate container, and forming said cap with an outwardly-extending ring, and in the outward end surface thereof forming an orienting means for controlled rotational movement;

forming a lower pull tab of a partially resilient material, said lower pull tab having a cavity sized and configured so as to removably grip the closed end of the concentrate container and particularly the extending ring and orienting means with and while a thickness of midportion envelope material is therebetween, and forming an upper pull tab of a partially resilient material, said upper pull tab having a cavity sized and configured so as to removably grip, rotate and tip a retained cap so as to remove by manipulation the resilient cap on the concentrate container, said cavity adapted to grip the extending ring and engage the orienting means formed in the cap with and while a thickness of a midportion envelope material is therebetween, and with manipulation the resilient cap is loosened and tipped so that said cap is removed with the upper and lower flexible midportions fluid-tight, and with the cap removed the concentrate contents are brought in way of the diluent in the envelope whereat mixing is achieved by shaking and the like, after which the mixed drug is removed from the container for use in a patient.

Terms such as "left," "right," "up," "down," "bottom," "top," "front," "back," "in," "out" and the like are applicable to the embodiments shown and described in conjunction with the drawings. These terms are merely for the purposes of description and do not necessarily apply to the position in which the drug-mixing device may be constructed or used.

While a particular embodiment of the drug-mixing device and an alternate embodiment of the upper pull tab have been shown and described, it is to be understood that the invention is not limited thereto and protection is sought to the broadest extent the prior art allows.

What is claimed is:

1. A drug-mixing device having an envelope adapted to receive and retain a determined quantity of diluent, said device adapted for isolation of the drug components during preparation, transporting, storage and, when mixing is desired, a manipulation and pulling is required to open a drug concentrate container for mixing of the contents of the envelope, after which withdrawal of the mixed drug from the envelope is made, this drug mixing device including:

(a) an envelope in which a desired quantity of a diluent is contained and in which at least upper and lower midportions of said envelope are of flexible material which is manipulable without rupture, said envelope substantially impervious to unwanted escape or seepage from said envelope of a fluid diluent retained therein;

(b) a fluid input and output fluid-conducting pathway member provided and secured to said envelope, said fluid-conducting path member adapted for carrying fluid to and from the envelope;

(c) a drug concentrate container carried within said envelope and of substantially rigid material and with said container having an open neck portion having means for retaining a removable cap member when seated thereon, said container having at or adjacent the closed end thereof an outwardly-extending ring portion and with an orienting means formed in the end of this container, this container end portion providing means for remotely grasping and providing controlled rotational movement of said container;

(d) a resilient cap or stopper carrier within said envelope, said cap having a retaining means when said cap is mounted on the neck of the concentrate container and when so mounted to retain the concentrate in an isolated and unmixed condition until said cap is removed from the container, said cap having an outwardly-extending retaining ring and having the outward end portion of said cap formed with orienting means, said ring and orienting means providing for controlled grasping, manipulation and rotational movement of said cap;

(e) a lower pull tab member that is partially resilient and formed so the lower portion of the concentrate container, the outwardly-extending ring portion and the orienting means therein when brought to a lower extent of the flexible midportion of the envelope are secured therebetween and the flexible midportion is retained absent rupture, and (f) an upper pull tab member that is partially resilient and is so formed that the formed cap with its outwardly-extending ring portion and the orienting means therein, when brought to the upper extent of the flexible midportion of the envelope and inserted into this upper grip member, said flexible midportion of the envelope is secured therebetween and is retained absent rupture, the upper and lower pull tab members manipulated so that the resilient cap member is loosened and tipped so that said cap is removed with the upper and lower flexible midportions fluid-tight, and with the cap removed the concentrate content are brought in way of the diluent in the envelope whereat mixing is achieved by shaking and the like, after which the mixed drug is removed from the container for use in a patient.

2. A drug-mixing device as in claim 1 in which the envelope is blow-molded and of flexible plastic, with end portions formed so as to provide gripping areas.

3. A drug-mixing device as in claim 2 in which the fluid input and output conducting pathway member is a neck portion integrally formed with the envelope and with the outer open end of said neck selectively closed by an attached impervious puncturable disc.

4. A drug-mixing device as in claim 1 in which the envelope is made from sheet plastic with sealed edges and ends, said ends formed with gripping areas.

5. A drug-mixing device as in claim 1 in which the drug concentrate container is a glass bottle, with the orienting means formed in the end as slot recess.

6. A drug-mixing device as in claim 5 in which the neck of the bottle is formed with an outwardly-extending ring and the resilient cap provided as a means for closing this drug concentrate container is formed with a mating retaining groove sized and positioned to snugly seat on the ring of the bottle.

7. A drug-mixing device as in claim 6 in which the resilient cap is formed with an internal surface which is provided with an impervious sealing film.

8. A drug-mixing device as in claim 7 in which the orienting means is a slot-like recess formed in said cap and sized to receive a mating tongue portion formed in and on the upper pull tab.

9. A drug-mixing device as in claim 1 in which the lower pull tab is formed with an outward flared end and the orienting device is a tongue member sized and adapted to seat in a slot formed in the closed end of the concentrate container.

10. A drug-mixing device as in claim 9 in which the lower pull tab is formed with a tapered chamfer leading from an outer surface to the recess for the retaining of the lower end of the drug concentrate container.

11. A drug-mixing device as in claim 1 in which the upper pull tab is formed with an extending portion adapted for grasping and manipulation, and particularly for tipping the resilient cap sufficiently for dislodgement and removal from the neck portion of the drug concentrate container.

12. A drug-mixing device as in claim 11 in which the upper pull tab is formed with an elongated manipulating portion adapted for grasping by the fingers of a hand and by these fingers to move the cap from the neck of a concentrate bottle.

13. A drug-mixing device as in claim 12 in which the upper pull tab is formed with a tapered chamfer leading from an outer surface to the recess for the retaining of said resilient cap.

14. A drug-mixing device as in claim 13 in which the upper pull tab is additionally provided with an attached loop member which provides grasping and manipulating means for removing the resilient cap from the concentrate container.

15. A drug-mixing device as in claim 1 in which the orienting means in the concentrate container and resilient cap are irregular recess configurations and the lower and upper pull tabs each have a compatibly-shaped orienting extending portion adapted to enter each of said recesses, with a flexible midportion therebetween.

16. A method of constructing a fluid storage device and mixing of a drug in which a diluent and concentrate are isolated during preparation, transporting and storage, the mixing requiring the removal of a resilient cap from a concentrate container and shaking the components to mix such drug, the construction of such device including the steps of:

(a) forming of plastic an envelope of a material that is substantially impervious to unwanted escape or seepage and sized to retain a desired quantity of diluent, said envelope also formed with lower and upper midportions of flexible thicknesses and material so that said midportions are deformable and manipulable without rupture;

(b) providing a fluid input and output pathway in said envelope so as to carry fluid to and from said envelope;

(c) carrying and positioning a drug concentrate container within said envelope, said container of substantially rigid material and having an open neck portion with cap retaining means formed on this neck portion, this container also having a closed end formed with an outwardly-extending ring portion and in this closed end forming an orienting means for controlled rotational movement;

(d) forming and providing a resilient cap or stopper and carrying said cap within the envelope, said cap formed with a retaining means compatible with and shaped to snugly engage and seat on the neck of the drug concentrate container, and forming said cap with an outwardly-extending ring, and in the outward end surface thereof forming an orienting means for controlled rotational movement;

(e) forming a lower pull tab of a partially resilient material, said lower pull tab having a cavity sized and configured so as to removably grip the closed end of the concentrate container and particularly the extending ring and orienting means with and while a thickness of midportion envelope material is therebetween, and (g) forming an upper pull tab of a partially resilient material, said upper pull tab having a cavity sized and configured so as to removably grip, rotate and tip a retained cap so as to remove by manipulation the resilient cap on the concentrate container, said cavity adapted to grip the extending ring and engage the orienting means formed in the cap with and while a thickness of a midportion envelope material is therebetween, and with manipulation the resilient cap is loosened and tipped so that said cap is removed with the upper and lower flexible midportions fluid-tight, and with the cap removed the concentrate contents are brought in way of the diluent in the envelope whereat mixing is achieved by shaking and the like, after which the mixed drug is removed from the container for use in a patient.

17. A method of constructing and mixing of a drug as in claim 16 which further includes forming the envelope with grasping areas by which the envelope may be shaken, and forming said envelope with a neck portion and with the outer end of said neck selectively closed by an attached impervious puncturable disc.

18. A method of constructing and mixing of a drug as in claim 17 which includes forming the concentrate container as a glass bottle with a reduced neck portion and an extending ring formed on the exterior of said neck.

19. A method of constructing and mixing of a drug as in claim 18 which includes the further steps of forming the lower pull tab with an outward flare and an inwardly-extending tongue which is configured so as to seat and engage orienting means formed in the closed end of the bottle, and also included forming the upper pull tab with an extending portion adapted for grasping, manipulation, and particularly for tipping and removal of the resilient cap from the concentrate bottle, and forming in said upper pull tab an inwardly-extending tongue which is adapted to seat in and engage the orienting means formed in the outer surface of the resilient cap.

20. A method of constructing and mixing of a drug as in claim 19 which includes the further step of forming the upper pull tab with an attached loop member which provides added grasping and manipulating means for rotating and removing the resilient cap from the concentrate bottle.

* * * * *